(12) United States Patent
Lenz

(10) Patent No.: US 7,144,420 B2
(45) Date of Patent: Dec. 5, 2006

(54) SEGMENTED SPINE

(75) Inventor: Jason T. Lenz, Maplewood, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 503 days.

(21) Appl. No.: 10/063,042

(22) Filed: Mar. 14, 2002

(65) Prior Publication Data
US 2003/0176913 A1    Sep. 18, 2003

(51) Int. Cl.
*A61F 2/06*    (2006.01)
(52) U.S. Cl. ..................................... 623/1.15
(58) Field of Classification Search .............. 623/1.15
See application file for complete search history.

(56) References Cited

U.S. PATENT DOCUMENTS

| | | | |
|---|---|---|---|
| 5,091,205 A | 2/1992 | Fan ............................. | 427/2 |
| 5,755,770 A | 5/1998 | Ravenscroft ................... | 623/1 |
| 5,800,526 A * | 9/1998 | Anderson et al. .......... | 623/1.16 |
| 5,824,046 A | 10/1998 | Smith et al. ................ | 623/1 |
| 5,843,120 A | 12/1998 | Israel et al. ................ | 606/198 |
| 5,957,930 A | 9/1999 | Vrba ........................... | 606/108 |
| 6,120,522 A | 9/2000 | Vrba et al. .................. | 606/190 |
| 6,123,712 A | 9/2000 | Di Caprio et al. .......... | 606/108 |
| 6,168,621 B1 | 1/2001 | Vrba ........................... | 623/1.2 |
| 6,270,524 B1 * | 8/2001 | Kim ........................... | 623/1.15 |
| 6,511,491 B1 * | 1/2003 | Grudem et al. ............. | 623/1.11 |
| 6,511,505 B1 * | 1/2003 | Cox et al. ................... | 623/1.16 |
| 6,540,777 B1 * | 4/2003 | Stenzel ....................... | 623/1.16 |
| 2002/0055770 A1 | 5/2002 | Doran et al. ................ | 623/1.15 |
| 2003/0018380 A1 * | 1/2003 | Craig et al. ................. | 623/1.15 |

FOREIGN PATENT DOCUMENTS

| | | | | |
|---|---|---|---|---|
| WO | 96/26689 | 9/1996 | | |
| WO | 00/30563 | 6/2000 | | |
| WO | 01/01889 | 1/2001 | | |
| WO | WO 01/01889 A1 * | 1/2001 | ............... | 623/1.15 |
| WO | 01/08600 | 2/2001 | | |

OTHER PUBLICATIONS

U.S. Appl. No. 60/238,178, filed Oct. 5, 2000, DiCaprio et al.
U.S. Appl. No. 60/234,548, filed Sep. 22, 2000, Girton et al.
U.S. Appl. No. 60/272,651, filed Mar. 1, 2001, Doran et al.
U.S. Appl. No. 60/272,906, filed Mar. 1, 2001, Doran et al.

* cited by examiner

Primary Examiner—Julian W. Woo
Assistant Examiner—Sarah Webb
(74) *Attorney, Agent, or Firm*—Vidas, Arrett & Steinkraus, P.A.

(57) ABSTRACT

A stent comprises a plurality of serpentine bands. Each serpentine band has alternating peak regions and trough regions and extends about substantially the entire circumference of the stent. At least one of the serpentine bands has a spline extending therefrom toward a serpentine band adjacent thereto. Serpentine bands which are adjacent one another are connected one to the other.

29 Claims, 2 Drawing Sheets

SEGMENTED SPINE

BACKGROUND OF THE INVENTION

Stents are placed or implanted within a blood vessel for treating stenoses, strictures or aneurysms therein. They are implanted to reinforce collapsing, partially occluded, weakened, or dilated sections of a blood vessel. They have also been implanted in other bodily vessels including arteries, veins, biliary ducts, urethras, fallopian tubes, bronchial tubes, the trachea and the esophagus.

Stents are typically either self-expanding or mechanically expandable via the application of radially outward force from within the stent, as by inflation of a balloon. An example of a balloon expandable stent is shown in U.S. Pat. No. 5,843,120. An example of a self-expanding stent is described in WO 96/26689. Hybrid stents, e.g. stents which are both self-expanding and mechanically expandable are also known. Examples of hybrid stents are disclosed in U.S. Pat. Nos. 6,168,621 and WO 01/08600.

Because stents are often delivered through tortuous vessels, it is important for a stent to have sufficient flexibility when in a delivery configuration. At the same time, it is desirable for a stent in an expanded configuration to exhibit sufficient scaffolding strength to maintain the patency of a vessel.

Although many stents have been designed with increased flexibility and scaffolding in mind, there remains a need for a stent which exhibits excellent flexibility and excellent scaffolding strength.

All US patents and all other published documents mentioned anywhere in this application are incorporated herein by reference in their entirety.

Without limiting the scope of the invention, a brief summary of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well for the purposes of complying with 37 C.F.R. 1.72.

SUMMARY OF INVENTION

In one embodiment, the invention is directed to a stent comprising a plurality of serpentine bands. Each serpentine band has alternating peak regions and trough regions and extends about substantially the entire circumference of the stent. At least one of the serpentine bands has a spline extending therefrom toward a serpentine band adjacent thereto and desirably, toward a reciprocating spline extending from a serpentine band adjacent thereto. Serpentine bands which are adjacent one another are connected one to the other. Desirably, at least one of the peak regions on one of the serpentine bands has a spline extending therefrom toward a reciprocating spline extending from a trough region on a serpentine band adjacent thereto.

Typically, splines will extend from a plurality of peak regions on one of the serpentine bands toward reciprocating splines which extend from trough regions on a serpentine band adjacent thereto. Also typically, splines will extend from peaks on more than one serpentine band with each spline extending toward a reciprocating spline which extends from a trough on an adjacent serpentine band. Desirably, every serpentine band has at least one spline or reciprocating spline extending therefrom.

The serpentine bands may be provided in any suitable arrangement. In one suitable arrangement, the serpentine bands comprise first serpentine bands and second serpentine bands. The first serpentine bands are of a first wavelength and amplitude and the second serpentine bands are of a second wavelength and amplitude less than the first wavelength and amplitude. The first and second serpentine bands alternate with one another along the length of the stent. First and second serpentine bands which are adjacent one another may be connected one to the other by one or more longitudinal connectors. Desirably, each longitudinal connector extends from a peak on a first serpentine band to a trough on a second serpentine band adjacent to the first serpentine band.

In many embodiments of the invention, the splines extend from the sides of peak regions and the reciprocating splines extend from the sides of trough regions.

Desirably, in an expanded configuration each spline contacts a trough region and each reciprocating spline contacts a peak region.

While the invention in its many embodiments contemplates any arrangement of splines and reciprocating splines, in one embodiment, a plurality of splines are in substantial longitudinal alignment with one another and a plurality of reciprocating splines are in substantial longitudinal alignment with one another.

The invention is also directed to a stent with at least one segmented spine. The stent comprises a plurality of serpentine bands which extend about substantially the entire circumference of the stent. Each serpentine band has a plurality of peak regions and a plurality of trough regions. At least some of the peak regions have splines extending therefrom toward trough regions. The segmented spine is formed of a plurality of peak regions with splines extending therefrom and trough regions longitudinally adjacent the splines. The segmented spine extends in a substantially longitudinal direction.

Additional details and/or embodiments of the invention are discussed below.

BRIEF DESCRIPTION OF THE DRAWINGS

FIG. 1b shows an enlargement of region 1b of FIG. 1a.
FIG. 1c shows an enlargement of region 1a of FIG. 1a.

DETAILED DESCRIPTION

Figure 1A:
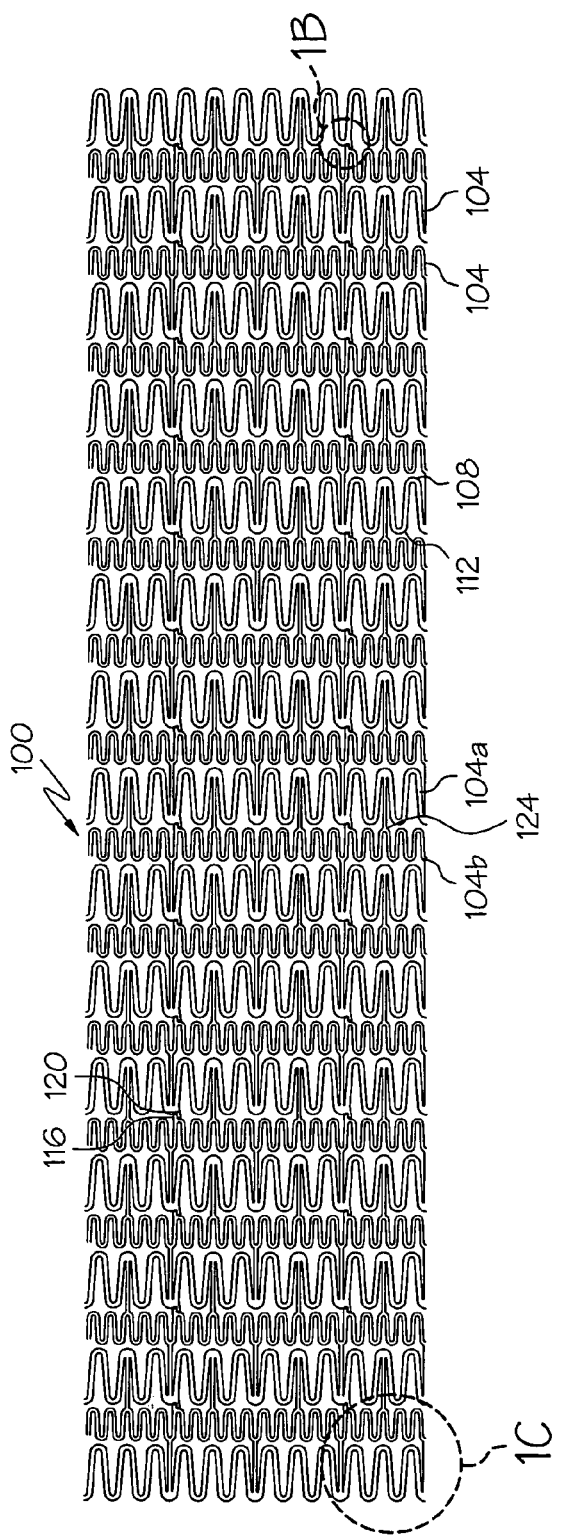
FIG. 1a shows a plan view of a flattened inventive stent.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1B:
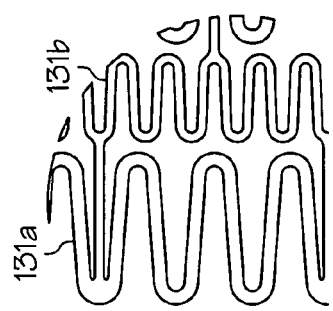
Figure 1C:
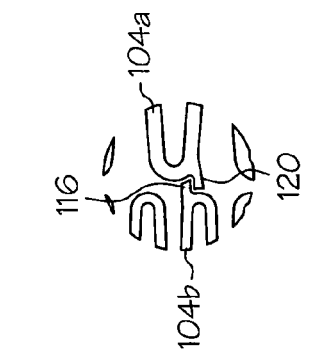

In one embodiment, the invention is directed to a stent shown generally at 100 in FIGS. 1a–c, comprising a plurality of serpentine bands 104. Each serpentine band has alternating peak regions 108 and trough regions 112 and extends about substantially the entire circumference of the stent. Serpentine bands 104 extend entirely about the circumference of the stent. The invention also contemplates circumferential serpentine bands with missing struts, where the bands extend about substantially the entire circumference of the stent.

At least one of the serpentine bands has a spline 116 extending therefrom toward a serpentine band adjacent thereto and desirably, toward a reciprocating spline 120 extending from a serpentine band adjacent thereto. Serpentine bands which are adjacent one another are connected one to the other. Desirably, as shown in FIG. 1a, at least one of the peak regions 108 on one of the serpentine bands has a spline 116 extending therefrom toward a reciprocating spline 120 extending from a trough region 112 on a serpentine band adjacent thereto.

Typically, as shown in FIG. 1a, splines will extend from a plurality of peak regions on one of the serpentine bands toward reciprocating splines which extend from trough regions on a serpentine band adjacent thereto. Also typically, splines will extend from peaks on more than one serpentine band with each spline extending toward a reciprocating spline which extends from a trough on an adjacent serpentine band. Desirably, every serpentine band has at least one spline or reciprocating spline extending therefrom.

The serpentine bands may be provided in any suitable arrangement, as shown in FIG. 1a, the serpentine bands comprise first serpentine bands 104a and second serpentine bands 104b. The first serpentine bands are of a first wavelength and amplitude and the second serpentine bands are of a second wavelength and amplitude less than the first wavelength and amplitude. Desirably, the first and second bands traverse paths about the circumference of the stent of equal length. First and second serpentine bands 104a and 104b alternate with one another along the length of the stent. First and second serpentine bands which are adjacent one another may be connected one to the other by one or more longitudinal connectors 124. Desirably, as shown in FIG. 1a, each longitudinal connector 124 extends from a peak region 108 on a first serpentine band 104a to a trough region 112 on a second serpentine band 104b adjacent to the first serpentine band.

Desirably, the splines will be spaced relatively close to adjacent trough regions and the reciprocating splines will be spaced relatively close to adjacent peak regions to minimize any foreshortening of the stent. In the embodiment of FIGS. 1a–c, the splines are separated from the trough regions by a gap of less than ⅓ of the longitudinal separation between the peak of the peak region of a serpentine band and the trough of the trough region of an adjacent serpentine band. Similarly, the reciprocal splines are separated from the peak regions by a gap of less than ⅓ of the longitudinal separation between the peak of a peak region of a serpentine band and the trough of the trough region of an adjacent serpentine band. The separation may be even smaller, on the order of ⅕ of the longitudinal separation between the peak of a peak region of a serpentine band and the trough of the trough region of an adjacent serpentine band or even smaller. Smaller gaps are particularly desirable in that they contribute to reduced foreshortening of the stent and also result in less pinching. Desirably, upon expansion of the stent, the splines rest against trough regions and the reciprocal splines rest against peak regions.

The gap may also be larger. Separations of up to ½ of the longitudinal separation between the peak of a peak region of a serpentine band and the trough of the trough region of an adjacent serpentine band are also within the scope of the invention.

The splines and reciprocal splines are desirably narrow relative to the struts that form the stent. They are also desirably narrow relative to the width of the peak regions and trough regions, respectively. In the embodiment of FIGS. 1a–1c, the splines are no wider than the width of the widest struts 131a and the reciprocal splines are no wider than the width of the narrowest struts 131b. Narrower splines may also be used. The width of the splines may also be such that the reciprocal splines are narrower than the widest struts and the splines are narrower than the narrowest struts. By using relatively narrow splines and reciprocal splines, one can avoid significantly increasing the crimped diameter of the stent.

The invention also contemplates the use of first serpentine bands of a first number of peaks and troughs and of a first longitudinal extent and second serpentine bands of a second number of peaks and troughs and of a second longitudinal extent where the first number of peaks and troughs exceeds the second number of peaks and troughs and where the first longitudinal extent exceeds the second longitudinal extent. Desirably, the first and second serpentine bands traverse paths about the circumference of the stent of equal length. Such a stent is shown at 100 in FIG. 1a. The invention also contemplates the use of first and second serpentine bands which traverse paths about the circumference of the stent of unequal length.

In many embodiments of the invention, including the embodiment of FIGS. 1a–c, the splines extend from the sides of peak regions and the reciprocating splines extend from the sides of trough regions. The invention also contemplates splines extending from the center of peak and trough regions. More generally, the splines and reciprocal splines may extend from any suitable position along the serpentine bands so long as they mate or key with one another. For example, the splines and reciprocal splines may extend from positions between peaks and troughs. In one embodiment, they may extend from positions midway between the peaks and troughs. In another embodiment, they may extend from positions closer to peaks and troughs.

The invention in its many embodiments contemplates any arrangement of splines and reciprocating splines. In one embodiment, a plurality of splines are in substantial longitudinal alignment with one another and a plurality of reciprocating splines are in substantial longitudinal alignment with one another to form one or more spines. The spines which are formed by longitudinally aligned splines and reciprocal splines provide for additional resistance against compression and yet allow for flexibility when the stent traverses a curved, tortuous pathway. When traversing a curve in a vessel, the spines on the outer part of the curve will tend to open as the splines and reciprocal splines move away from the trough regions and peak regions. The spines on the inner part of the curve will tend to compress.

The use of splines as disclosed herein is of particular utility in stents of open cell construction having adjacent serpentine bands which include peaks and troughs which are not directly connected one to the other. The invention also contemplates the use of splines in closed cell stents. In such embodiments, splines extend from all of the peak regions toward trough regions on adjacent serpentine bands.

Figure 2:
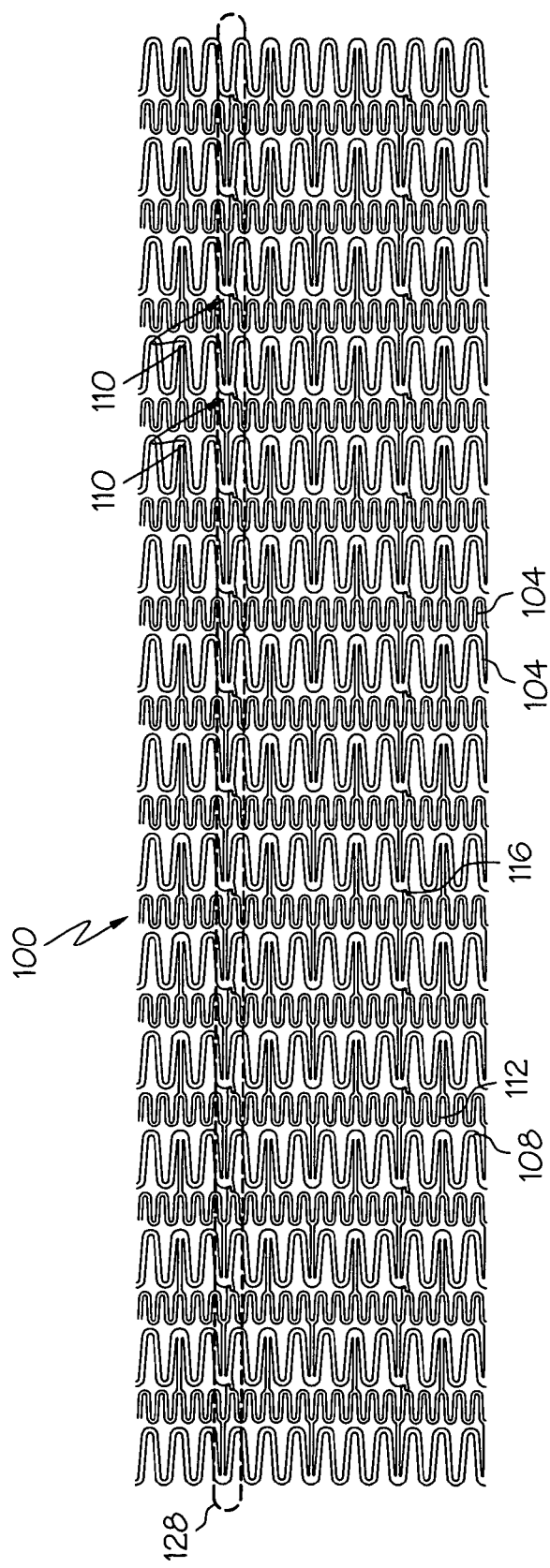
FIG. 2 shows the stent of FIG. 1 with a segmented spine highlighted.

The invention is also directed to a stent with at least one segmented spine. The stent, shown at 100 in FIG. 2, comprises a plurality of serpentine bands 104 which extend circumferentially about the stent. Each serpentine band has a plurality of peak regions 108 and a plurality of trough regions 112. At least some of the peak regions have splines 116 extending therefrom toward trough regions. The segmented spine, one of which is shown highlighted at 128, comprises a plurality of peak regions with splines extending therefrom and trough regions longitudinally adjacent the splines. The segmented spine desirably extends in a substantially longitudinal direction. As shown in FIG. 2, the segmented spine may optionally extend from one end of the stent to the other end of the stent. Optionally, in other embodiments of the invention, the segmented spine extend only over a part of the stent. For example, in one embodiment, the segmented spine extends only in a middle region of the stent. In another embodiment, the segmented spine extends less than the entire length of the stent, starting from one end of the stent.

Stents in accordance with the instant invention may be provided with a single segmented spine or, as shown in FIG. 2, with a plurality of segmented spines.

Typically, as shown in FIG. 2, serpentine bands which are adjacent one another are connected one to the other via a plurality of longitudinal connectors and one or more of the longitudinal connectors will form part of the segmented spine.

Any of the inventive stents disclosed above may be provided with a uniform diameter or may taper in portions or along the entire length of the stent. Also, the width and/or thickness of the various portions of the inventive stents may increase or decrease along a given portion of the stent. For example, the width and/or thickness of the circumferential serpentine bands and/or connectors may increase or decrease along portions of the stent or along the entire length of the stent. The longitudinal extent and number of peaks and troughs of several successive serpentine bands may remain constant while the width and/or thickness of the successive serpentine bands decreases. Similarly, the longitudinal extent and number of peaks and troughs of several successive serpentine bands may remain constant while the width and/or thickness of the successive serpentine bands decreases.

The inventive stents may also be modified, by choice of material or geometry so that one or both ends are more rigid or more flexible than the remainder of the stent.

The inventive stents may be manufactured using known stent manufacturing techniques. Suitable methods for manufacturing the inventive stents include laser cutting, chemical etching or stamping of a tube. The inventive stents may also be manufactured by laser cutting, chemically etching, stamping a flat sheet, rolling the sheet and, optionally, welding the sheet. Other suitable manufacturing techniques include electrode discharge machining or molding the stent with the desired design. The stent may also be manufactured by welding individual sections, for example, circumferential bands, together. Any other suitable stent manufacturing process may also be used.

The inventive stents may also be made from a single piece of material. For example, a sheet of super-elastic material or any other suitable material may be provided and a stent pattern provided therein by laser cutting, etching, mechanical cutting or any other suitable method. The sheet of material may then be rolled to form a stent. Optionally, opposing edges of the sheet may be welded or otherwise joined to one another. The coil portion may then be straightened. Upon insertion of the stent in the body and expansion of the stent, the coil portion will assume its coil configuration.

The inventive stents may likewise be made from a tube. The tube is provided with a stent design, as by laser cutting etching, mechanical cutting and the like.

The inventive stents may find use in the cerebral arteries as well as in the coronary arteries, renal arteries, the peripheral arteries including iliac arteries, and arteries of the neck.

The stents of the present invention, however, are not limited to use in the vascular system and may also be advantageously employed in other body structures, including but not limited to arteries, veins, biliary ducts, urethras, fallopian tubes, bronchial tubes, the trachea, the esophagus and the prostate. The inventive stents may be used interarterially in the brain, deployed across the neck of an aneurysm as well as in occlusions in bodily vessels. The size of the inventive stents will be appropriate for the intended usage of the stent.

Any suitable stent material may be used in the manufacture of the inventive stents. Examples of such materials include polymeric materials, metals, ceramics and composites. Suitable polymeric materials include thermotropic liquid crystal polymers (LCP's). Where the stent is made of metal, the metal may be stainless steel, cobalt chrome alloys such as elgiloy, tantalum or other plastically deformable metals. Other suitable metals include shape-memory metals including nickel-titanium alloys generically known as "nitinol", platinum/tungsten alloys and titanium alloys.

The invention also contemplates the use of more than one material in the inventive stents. For example, the serpentine bands may be made of different materials. Optionally, the connectors may be made of a different material than the serpentine bands.

The inventive stents may be provided in mechanically expandable form, in self-expanding form or as a hybrid of the two. Mechanically expandable stents, in accordance with the invention, may be expanded using any suitable mechanical device including a balloon.

The inventive stents may include suitable radiopaque coatings. For example, the stents may be coated with gold or other noble metals or sputtered with tantalum or other metals. The stents may also be made directly from a radiopaque material to obviate the need for a radiopaque coating or may be made of a material having a radiopaque inner core. Other radiopaque metals which may be used include platinum, platinum-tungsten, palladium, platinum-iridium, rhodium, tantalum, or alloys or composites of these metals.

The inventive stents may also be provided with various bio-compatible coatings to enhance various properties of the stent. For example, the inventive stents may be provided with lubricious coatings. The inventive stents may also be provided with drug-containing coatings which release drugs over time.

The inventive stents may also be provided with a sugar or more generally a carbohydrate and/or a gelatin to maintain the stent on a balloon during delivery of the stent to a desired bodily location. Other suitable compounds for treating the stent include biodegradable polymers and polymers which are dissolvable in bodily fluids. Portions of the interior and/or exterior of the stent may be coated or impregnated with the compound. Mechanical retention devices may also be used to maintain the stent on the balloon during delivery. To that end, the use of other coatings on the inventive stents is also within the scope of the invention.

The coating may comprise one or more non-genetic therapeutic agents, genetic materials and cells and combinations thereof as well as other polymeric coatings.

Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/ anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms.

Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor, cell cycle inhibitors including CD inhibitors, thymidine kinase ("TK") and other agents useful for interfering with cell proliferation the family of bone morphogenic proteins ("BMP's"), BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Cells can be of human origin (autologous or allogeneic) or from an animal source (xenogeneic), genetically engineered if desired to deliver proteins of interest at the transplant site. The cells may be provided in a delivery media. The delivery media may be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL®), fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone.

The inventive stents may also be used as the framework for a graft. Suitable coverings include nylon, collagen, PTFE and expanded PTFE, polyethylene terephthalate and KEVLAR, or any of the materials disclosed in U.S. Pat. Nos. 5,824,046 and 5,755,770. More generally, any known graft material may be used including synthetic polymers such as polyethylene, polypropylene, polyurethane, polyglycolic acid, polyesters, polyamides, their mixtures, blends and copolymers.

The invention is also directed to the combination of an inventive stent disclosed herein disposed on a catheter. Suitable catheter such as those disclosed in U.S. Pat. Nos. 6,123,712, 6,120,522 and 5,957,930 may be used to deliver the inventive stents to the desired bodily location. The choice of delivery device will depend on whether a self-expanding or balloon expandable stent is used. The inventive stents may be delivered in conjunction with one or more stent retaining sleeves. An example of stent retaining sleeves is disclosed in U.S. provisional application No. 60/2381 78. Desirably, where an inventive self-expanding stent is used, the stent has a restraining sheath disposed thereabout. Additional details concerning the catheter may be found in U.S. Pat. No. 5,957,930.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 4 may be taken as alternatively dependent from claims 1 or 2; claim 5 may depend from any of claims 1–4; claim 6 may be taken as alternatively dependent from any of claims 2–5; etc.).

This completes the description of the preferred and alternate embodiments of the invention. Those skilled in the art may recognize other equivalents to the specific embodiment described herein which equivalents are intended to be encompassed by the claims attached hereto.

The invention claimed is:

1. A stent comprising a plurality of serpentine bands, each serpentine band having alternating peak regions and trough regions and extending about substantially the entire circumference of the stent, at least one of the serpentine bands having a peak having a single spline extending therefrom toward a serpentine band adjacent thereto, the spline extending from a side of said peak, the spline and adjacent band separated by a gap, the adjacent band having a reciprocating spline extending therefrom, serpentine bands which are adjacent one another connected one to the other, wherein the spline and the reciprocating spline both cross a common stent circumference.

2. The stent of claim 1 wherein the spline extends toward the reciprocating spline.

3. The stent of claim 2 wherein the reciprocating spline extends from a trough region.

4. The stent of claim 3 wherein splines extend from a plurality of peak regions on one of the serpentine bands toward reciprocating splines extending from trough regions on a serpentine band adjacent thereto.

5. The stent of claim 4 wherein splines extend from peak regions on more than one serpentine band, each spline extending toward a reciprocating spline extending from a trough region on an adjacent serpentine band.

6. The stent of claim 3 wherein every serpentine band has at least one spline or reciprocating spline extending therefrom.

7. The stent of claim 3 wherein the serpentine bands comprise first serpentine bands and second serpentine bands, the first serpentine bands of a first wavelength and amplitude and the second serpentine bands of a second wavelength and amplitude less than the first wavelength and amplitude, the first and second serpentine bands alternating with one another along the length of the stent.

8. The stent of claim 7 wherein first and second serpentine bands which are adjacent one another are connected one to the other by one or more longitudinal connectors.

9. The stent of claim 8 wherein each longitudinal connector extends from a peak region on a first serpentine band to a trough region on a second serpentine band adjacent to the first serpentine band.

10. The stent of claim 9 wherein the splines extend from sides of peak regions and the reciprocating splines extend from sides of trough regions.

11. The stent of claim 8 wherein a plurality of splines are in substantial longitudinal alignment with one another and a plurality of reciprocating splines are in substantial longitudinal alignment with one another.

12. The stent of claim 1 wherein the spline extends from the peak region toward a trough region.

13. The stent of claim 12 wherein splines extend from a plurality of peak regions on one of the serpentine bands toward trough regions on a serpentine band adjacent thereto.

14. The stent of claim 12 wherein splines extend from peak regions on more than one serpentine band, each spine extending toward a trough region on an adjacent serpentine band.

15. The stent of claim 14 wherein reciprocating splines extend from trough regions on at least some of the serpentine bands toward peak regions on adjacent serpentine bands.

16. The stent of claim 15 wherein every serpentine band has at least one spline or reciprocating spline extending therefrom.

17. The stent of claim 15 wherein the serpentine bands comprise first serpentine bands and second serpentine bands, the first serpentine bands of a first wavelength and amplitude and the second serpentine bands of a second wavelength and amplitude less than the first wavelength and amplitude, the first and second serpentine bands alternating with one another along the length of the stent.

18. The stent of claim 17 wherein first and second serpentine bands which are adjacent one another are connected one to the other by one or more longitudinal connectors.

19. The stent of claim 18 wherein each longitudinal connector extends from a peak region on a first serpentine band to a trough region on a second serpentine band adjacent to the first serpentine band.

20. The stent of claim 19 wherein the splines extend from sides of peak regions and the reciprocating splines extend from sides of trough regions.

21. The stent of claim 17 wherein a plurality of splines are in substantial longitudinal alignment with one another and a plurality of reciprocating splines are in substantial longitudinal alignment with one another.

22. A stent comprising a plurality of serpentine bands which extend substantially about the entire circumference of the stent, each serpentine band having a plurality of peak regions and a plurality of trough regions, at least some of the peak regions having splines extending therefrom toward trough regions adjacent thereto, at least one peak region having a single spline extending from a side of the peak region, at least one trough region having a reciprocating spline extending therefrom, each spline terminating short of the trough toward which it extends to form a gap between the spline and the trough, a plurality of splines being aligned in a longitudinal direction, wherein the reciprocating spline and at least one spline both cross a common stent circumference.

23. The stein of claim 22 wherein a segmented spine extends from one end of the stent to the other end of the stent.

24. The stent of claim 22 wherein serpentine bands which are adjacent one another are connected one to the other via a plurality of longitudinal connectors.

25. The stern of claim 24 wherein one or more longitudinal connectors form part of a segmented spine.

26. The stout of claim 22 wherein at least some of the splines are adjacent to reciprocating splines, splines and reciprocating splines which are adjacent one another being separated by a gap and extending from peaks and troughs which face one another.

27. The stent of claim 2 wherein splines and reciprocating splines which are adjacent thereto are separated one from the other by a gap.

28. A stent having an expanded configuration and an unexpanded configuration, the stent comprising a plurality of serpentine bands, each serpentine band having alternating peak regions and trough regions and extending about substantially the entire circumference of the stent, serpentine bands which are adjacent one another connected one to the other, at least one of the serpentine bands comprising a peak having a single spline extending therefrom toward a serpentine band adjacent thereto, the spline extending from a side of said peak, wherein the spline and adjacent band are separated by a gap in the unexpanded configuration, and wherein said spline contacts a trough region of said serpentine band adjacent thereto in the expanded configuration.

29. The stent of claim 28, wherein said spline extends toward a reciprocating spline extending from said serpentine band adjacent thereto, wherein in the expanded configuration said reciprocating spine contacts a peak region.

* * * * *